United States Patent
Banks et al.

(10) Patent No.: US 6,387,915 B2
(45) Date of Patent: May 14, 2002

(54) ISOXAZOLE-SULFONAMIDE ENDOTHELIN ANTAGONISTS

(75) Inventors: Bernard Joseph Banks; Nathan Anthony Logan Chubb; James John Eshelby; Michael Stephen Pacey, all of County of Kent (GB); Darren John Schulz, Groton, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/867,488

(22) Filed: May 30, 2001

Related U.S. Application Data

(60) Provisional application No. 60/220,285, filed on Jul. 24, 2000, and provisional application No. 60/230,112, filed on Sep. 5, 2000.

(30) Foreign Application Priority Data

May 31, 2000 (GB) .............................................. 0013368
Jul. 26, 2000 (GB) .............................................. 0018356

(51) Int. Cl.[7] .................... C07D 261/12; C07D 239/46; A61K 31/42; A61K 31/505
(52) U.S. Cl. ...................... 514/274; 548/244; 514/380; 544/315
(58) Field of Search .......................... 548/244; 514/380, 514/274; 544/315

(56) References Cited

U.S. PATENT DOCUMENTS

| | | | |
|---|---|---|---|
| 5,589,478 A | 12/1996 | Yamada et al. | 514/269 |
| 5,739,333 A | 4/1998 | Yamada et al. | 544/296 |
| 5,856,484 A | 1/1999 | Breu et al. | 544/319 |
| 5,883,092 A | 3/1999 | Hirata | 514/235.8 |
| 5,962,682 A | 10/1999 | Breu et al. | 544/123 |
| 6,004,965 A | 12/1999 | Breu et al. | 514/256 |
| 6,008,224 A | 12/1999 | Hirata et al. | 514/269 |
| 6,083,955 A | 7/2000 | Harada et al. | 514/269 |

FOREIGN PATENT DOCUMENTS

| | | |
|---|---|---|
| EP | 0713875 | 3/2001 |
| JP | 09059160 | 3/1997 |
| JP | 10194972 | 7/1998 |
| JP | 10226649 | 8/1998 |
| WO | WO9711942 | 4/1997 |
| WO | WO9803488 | 1/1998 |
| WO | WO9936408 | 8/1998 |
| WO | WO9857938 | 12/1998 |
| WO | WO0117976 | 3/2001 |

Primary Examiner—Richard L. Raymond
Assistant Examiner—Hong Liu
(74) Attorney, Agent, or Firm—Peter C. Richardson; Gregg C. Benson; Arlene K. Musser

(57) ABSTRACT

Isoxazole-sulfonamide endothelin antagonists of formula (I) below having good affinity for endothelin receptors and selectivity for $ET_A$ over $ET_B$ are described herein.

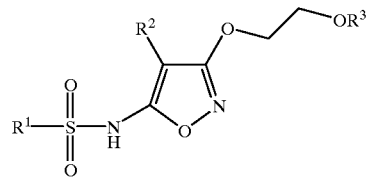

(I)

Such compounds are useful in the treatment of conditions mediated by endothelin, in particular, conditions mediated by endothelin $ET_A$.

32 Claims, No Drawings

ISOXAZOLE-SULFONAMIDE ENDOTHELIN ANTAGONISTS

This application claims the benefit of U.S. Provisional Patent Application Nos. 60/220,285 filed Jul. 24, 2000, and 60/230,112 filed Sep. 5, 2000, both of which are incorporated herein by reference.

FIELD OF THE INVENTION

This invention relates to isoxazole derivatives useful in the treatment of a variety of conditions mediated by endothelin and to pharmaceutical formulations containing such compounds useful for the treatment of humans and non-human mammals.

BACKGROUND

Endothelin (ET) is a potent vasoconstrictor synthesized and released by endothelial cells. There are three distinct isoforms of ET: ET-1, ET-2 and ET-3, all being 21-amino acid peptides and herein the term 'endothelin' refers to any or all of the isoforms. Two receptor subtypes, $ET_A$ and $ET_B$ have been pharmacologically defined (see for example H. Arai et al., Nature, 348, 730, 1990) and further subtypes have recently been reported. Stimulation of $ET_A$ promotes vasoconstriction and stimulation of $ET_B$ receptors causes either vasodilation or vasoconstriction. The main effects of ET are observed in the cardiovascular system, particularly in the coronary, renal, cerebral and mesenteric circulation, and the effects of endothelin are often long-lasting. Stimulation of ET receptors also mediate further biological responses in cardiovascular and non-cardiovascular tissues such as cell proliferation and matrix formation.

Increased circulating levels of endothelin have been observed in patients who have undergone percutaneous transluminal coronary angioplasty (PTCA) (A. Tahara et al.,Metab. Clin. Exp. 40, 1235, 1991) and ET-1 has been found to induce neointimal formation in rats after balloon angioplasty (S. Douglas et al., J.Cardiovasc. Pharm., 22 (Suppl 8), 371, 1993). The same workers have found that an endothelin antagonist, SB-209670, causes a 50% reduction in neointimal formation relative to control animals (S. Douglas et al., Circ. Res, 75, 1994). Antagonists of the endothelin receptor may thus be useful in preventing restenosis post PTCA. The $ET_{A/B}$ receptor antagonist Bosentan reportedly decreased blood pressure in hypertensive patients (H. Krum et al., New Eng. J. Med. (1998) 338, 784–790). Antagonists of $ET_B$ receptors such as BQ-788 have been demonstrated to increase peripheral resistance in man (Hypertension (1999) 33, 581–585). Thus $ET_A$-selective receptor antagonists are of benefit in hypertension.

Endothelin-1 is produced in the human prostate gland and endothelin receptors have been identified in this tissue (Y. Saita et al., Eur. J. Pharmacol. (1988) 349, 123–128). Since endothelin is a contractile and proliferative agent, endothelin antagonists are useful in the treatment of benign prostate hypertrophy.

There is widespread localization of endothelin and its receptors in the central nervous system and cerebrovascular system (R. K. Nikolov et al., Drugs of Today, 28(5), 303, 1992) with ET being implicated in cerebral vasospasm, cerebral infarcts, septic shock, myocardial infarction and neuronal death.

Elevated levels of endothelin have also been observed in patients with:

recurrent airway obstruction (Pulm. Pharm. Ther., (1998) 11: 231–235);

asthma (Am. J. Resp. Crit. Care Med., (1995) 151:1034–1039);

acute renal failure (K. Tomita, et al, Med. Philos. (1994) 13(1), 64–66);

chronic renal failure (F. Stockenhuber et al., Clin. Sci. (Lond.), 82, 255, 1992);

ischaemic Heart Disease (M. Yasuda, Am. Heart J., 119, 801, 1990);

stable or unstable angina (J. T. Stewart, Br. Heart J., 66, 7 1991);

pulmonary hypertension (D. J. Stewart et al., Ann. Internal Medicine, 114, 464, 1991);

congestive heart failure (R. J. Rodeheffer et al., Am. J Hypertension, 4, 9A, 1991);

preeclampsia (B. A. Clark et al.,Am. J. Obstet. Gynecol., 166, 962, 1992);

diabetes (A. Collier et al., Diabetes Care, 15 (8), 1038, 1992);

Crohn's disease (S. H. Murch et al., Lancet, 339, 381, 1992); and atherosclerosis (A. Lerman et al., New Eng. J. Med., 325, 997, 1991).

In every case the disease state associated with the physiologically elevated levels of endothelin is potentially treatable with a substance which decreases the effect of endothelin, such as an endothelin receptor antagonist, or a compound which binds endothelin such that it reduces the effective concentration thereof at the endothelin receptors.

Compounds that antagonize the $ET_A$ receptor to a greater extent than the $ET_B$ receptor are preferred as $ET_A$ receptors are predominantly present in vascular smooth muscles. Blockade of $ET_B$ receptor activation may reverse endothelial dependent vasodilation which is beneficial in hypertension. ET may also mediate regeneration of damaged tissue via the $ET_B$ receptor, such as proximal tubule cells in the kidney. Thus blockade of $ET_B$ receptors, e.g. with a non-selective ET antagonist could inhibit tissue repair. $ET_B$ receptors are also involved in the clearance of ET from the systemic circulation. Increased levels of ET are generally considered detrimental. Rises in circulating levels have been observed with non-selective ET antagonists. Treatment with selective $ET_A$ receptor antagonists is not likely to induce such rises in circulating levels.

There are a number of publications relating to N-(pyrimidin-4-yl)sulphonamide derivatives having endothelin binding/antagonist activity, for example EP-A-0743307, EP-A-0658548, EP-A-0633259, EP-A-0882719, WO-A-96/20177, EP-A-15 0801062, WO-A-97/09318, EP-A-0852226, EP-A-0768304, WO-A-96/19459, WO-A-98/03488, WO-A-98/57938, WO-A-99/36408, WO-A-01/17976 and EP-A-0713875.

Various N-4-pyrimidinyl sulphonamide derivatives possessing endothelin antagonist activity are described in EP-A-0882719, JP-A-09059160, JP-A-1 0194972 and JP-A-1 0226649.

International Patent Application publication number WO-A-96/19455 discloses phenyl and pyridin-4-yl sulphonamides as endothelin antagonists.

International Patent Application publication number WO-A-97/11942 discloses various (4-arylthioisoxazol-3-yl) sulphonamides, with an aldehyde moiety linked to the 5-position of the isoxazole ring, as selective $ET_B$ receptor selective antagonists.

SUMMARY OF THE INVENTION

We have unexpectedly found that isoxazoles of formula (I) below have good affinity for endothelin receptors, and are selective for $ET_A$ over $ET_B$.

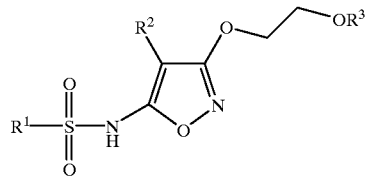

wherein
R¹ is
a) a phenyl group,
b) a 5- or 6-membered heterocyclic group containing one to three heteroatoms each independently selected from the group consisting of N, O and S, said heterocyclic group being optionally fused to a benzo group,
c) CHR⁶CHR⁷Ph, or
d) CR⁶=CR⁷Ph,
where groups (a) (b) and (c) are optionally each independently substituted with one to three substituents selected from the group consisting of halo, $C_{1-6}$ alkyl optionally substituted by OH, halogen, NR⁴R⁵, OCOR⁴, CO₂R⁴, CN, O($C_{1-6}$ alkyl optionally substituted by one or more halogens), and CO₂R⁴, where R⁴ and R⁵ are each independently H or $C_{1-6}$ alkyl optionally substituted by one or more halo, and R⁶ and R⁷ are each independently H or $C_{1-3}$ alkyl;

R² is aryl¹ or het¹; and
R³ is H, $C_{1-6}$ alkyl, C(O)R⁴, CONHaryl¹, CONHhet¹, aryl¹ and het¹;
where aryl¹ is a phenyl or a naphthyl group, said phenyl and said naphthyl groups being optionally substituted with one to three substituents each independently selected from the group consisting of $C_{1-3}$ alkyl, CF₃, halo, $C_{1-3}$ alkoxy, OCF₃, OH, NO₂, CN, NR⁴R⁵, COR⁴, CO₂R⁴, CONR⁴R⁵, S(O)$_p$($C_{1-3}$ alkyl), CH₂NR⁴COR₅, COCF₃, CH₂OH, S(O)$_p$CF₃, C(=NH)NH₂, $C_{2-3}$ alkynyl, $C_{2-3}$ alkenyl, phenyl and het²,
het¹ is a 5- to 7-membered fully saturated, partially unsaturated, or fully unsaturated heterocyclic group containing one to three hetero-atoms each independently selected from the group consisting N, O and S, said heterocyclic group being optionally fused to a benzo group and optionally substituted with one to three substituents each independently selected from the group consisting of $C_{1-3}$ alkyl, CF₃, halo, $C_{1-3}$ alkoxy, CF₃O, OH, NO₂, CN, NR⁴R⁵, COR⁴, CO₂R⁴, CONR⁴R⁵, S(O)$_p$($C_{1-3}$ alkyl), CH₂NR⁴R⁵, NR⁴COR⁵, COCF₃, CH₂OH, S(O)$_p$CF₃, C(=NH)NH₂, $C_{2-3}$ alkynyl, $C_{2-3}$ alkenyl, phenyl and het², with the proviso that when R³ is het¹, the het¹ group is linked to the adjacent O atom by a carbon atom,
het² is a 5- to 7-membered fully saturated, partially unsaturated, or fully unsaturated heterocyclic group containing one to three hetero-atoms each independently selected from the group consisting of N, O and S,
and p is 0, 1 or 2;
or a pharmaceutically acceptable derivative thereof.

The term "pharmaceutically acceptable derivatives" refers to prodrugs of the compounds of Formula (I) as well as the pharmaceutically acceptable salts, hydrates and solvates of the compounds of Formula (I) and prodrugs thereof. For example, pharmaceutically acceptable derivatives include those compounds in which the functional groups explicitly recited above have been derivatized to provide prodrugs which can be converted to the parent compound in vivo. Such prodrugs are discussed in *Drugs of Today*, Vol. 19, 499–538 (1983) and *Annual Reports in Medicinal Chemistry*, Vol. 10, Ch. 31 p306–326. The term pharmaceutically acceptable derivatives also includes veterinarily acceptable derivatives and any zwitterionic or tautomeric species that may exist.

"Halo" means fluoro, chloro, bromo or iodo.
Alkyl, alkenyl and alkynyl groups may be straight chain, branched or cyclic where the number of carbon atoms allows.
Preferably R¹ is either
a) a phenyl group, or
b) a 5–7 membered heterocyclic group containing 1–3 heteroatoms each independently selected from the group consisting of O, S and N;
the phenyl and the heterocyclic groups may be optionally substituted by 1–3 substituents each independently selected from the group consisting of halo and $C_{1-6}$ alkyl optionally substituted by OH or CO₂H.
More preferably R¹ is a phenyl group optionally substituted by $C_{1-6}$ alkyl, where the $C_{1-6}$ alkyl group is optionally substituted by OH or CO₂H.
Most preferably R¹ is phenyl substituted at the 4 position by t-butyl or 2-hydroxy-1,1-dimethylethyl.
Preferably R² is either
a) a phenyl group or
b) a 5–7 membered heterocyclic group containing 1–3 heteroatoms each independently selected from the group consisting of O, S and N, where the heterocyclic group is optionally fused to a benzo group, and the phenyl and heterocyclic groups are optionally substituted by 1–3 substituents selected from the group consisting of halogen and $C_{1-6}$ alkyl optionally substituted by OH or CO₂H.
More preferably R² is benzodioxol or 4-methylphenyl.
Most preferably R² is a 1,3-benzodiox-5-ol.
Preferably R³ is hydrogen, $C_{1-6}$ alkyl, C(O)$C_{1-6}$ alkyl, phenyl, or a 5–7 membered heterocyclic group containing 1–3 heteroatoms each independently selected from the group consisting of O, S and N, where the heterocyclic group is optionally fused to a benzo group, and the phenyl and the heterocyclic groups are optionally substituted by halo, ($C_{1-5}$ alkyl)OH, ($C_{1-5}$ alkyl)CO₂H, or SO$_p$R⁴, where p is 0, 1 or 2.
More preferably R³ is hydrogen, C(O)CH₃, or a pyrimidine optionally substituted by chloro, bromo, ($C_{1-5}$ alkyl)OH, ($C_{1-5}$ alkyl)CO₂H, or SO$_p$CH₃, where p is 0, 1 or 2.
Most preferably R³ is 4-chloropyrimidinyl
Preferably R⁴ and R⁵ are hydrogen or $C_6$ alkyl.
More preferably R⁴ and R⁵ are hydrogen or $C_{1-6}$ alkyl.
Most preferably R⁴ and R⁵ are CH₃.
Preferably R⁶ and R⁷ are hydrogen or CH₃.
More preferably R⁶ and R⁷ are hydrogen.
Preferred sets of compounds are those described in the Examples and pharmaceutical derivatives thereof.
Most preferred are the compounds:
N-(4-(1,3-benzodioxol-5-yl)-3-{2-[(5-chloro-2-pyrimidinyl) oxy]ethoxy}-5-isoxazolyl)-4-(tert-butyl) benzenesulfonamide;
N-(4-(1,3-benzodioxol-5-yl)-3-{2-[(5-bromo-2-pyrimidinyl) oxy]ethoxy}-5-isoxazolyl)-4-(tert-butyl) benzenesulfonamide; or N-(4-(1,3-benzodioxol-5-yl)-3-{2-[(5-bromo-2-pyrimidinyl)oxy]ethoxy}-5-isoxazolyl)-4-(2-hydroxy-1,1-dimethylethyl)benzenesulfonamide.

The compounds of the present invention may possess one or more chiral centers and so exist in a number of stereoisomeric forms. All stereoisomers and mixtures thereof are included in the scope of the present invention. Racemic substances may either be separated using preparative HPLC and a column with a chiral stationary phase or resolved to yield individual enantiomers utilizing methods known to those skilled in the art. In addition, chiral intermediates may be resolved and used to prepare chiral compounds of formulae (IA) and (IB).

The compounds of the invention are useful because they blockade ET receptors and are thus useful in the treatment or prevention of any diseases for which such a blockade is beneficial. More particularly, they are useful in the treatment and prevention of restenosis, acute/chronic renal failure, hypertension including pulmonary and systemic hypertension; benign prostatic hypertrophy, male erectile dysfunction, prostate cancer, metastatic bone cancer, congestive heart failure, stroke, subarachnoid haemorrhage, angina, atherosclerosis, cerebral and cardiac ischaemia, prevention of ischaemia/reperfusion injury (e.g. allografts), cyclosporin induced nephrotoxicity, glaucoma, radiocontrast nephropathy, diabetic neuropathy, allergy, restoration of organ perfusion in haemorrhagic shock, lipoprotein lipase related disorders, chronic obstructive pulmonary disease and hyaline membrane disease in newborn. The treatment of congestive heart failure, restenosis, renal failure and systemic and pulmonary hypertension are of particular interest. The compounds of the present invention may be administered alone or as part of a combination therapy.

The present invention further provides methods for the production of the compounds of the invention, which are described below and in the Examples and Preparations section.

DETAILED DESCRIPTION

One skilled in the art will appreciate that the compounds of the present invention can be made by methods other than those herein described, by adaptation of the methods herein described and/or adaptation of a plethora of methods known in the art. It is to be understood that the synthetic transformation methods specifically mentioned herein may be carried out in various different sequences in order that the desired substances can be efficiently assembled. The skilled chemist will exercise his judgement and skill as to the most efficient sequence of reactions for synthesis of a given target compound.

It will be apparent to those skilled in the art that sensitive functional groups may need to be protected and deprotected during synthesis of a substance of the invention. This may be achieved by conventional techniques, for example as described in "Protective Groups" in *Organic Synthesis* by T W Greene and P G M Wuts, John Wiley and Sons Inc, 1991.

In the Methods below, unless otherwise specified, the substituents are as defined above with reference to the compounds of formula (I) above.

Method 1

Compounds of formula (I) can be made via reaction of the corresponding compound of formula (II) as appropriate,

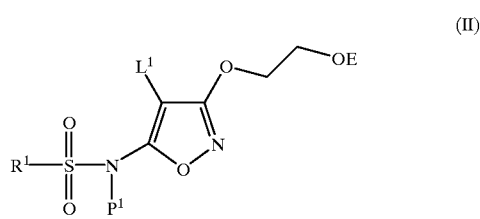

(II)

where $L^1$ is a leaving group such as Cl, Br, I or triflate, $P^1$ is H, $R^1SO_2$ or a nitrogen-protecting group such as methoxymethyl, iso-butoxycarbonyl, etc., and E is $R^3$ as defined with reference to compounds of formula (I) above, or E is a suitable oxygen-protecting group such as ($C_{1-4}$ alkyl)CO, with a reagent which is equivalent to $R^2$—Y. For instance the reagent $R^2$—Y can be an organometallic species such as an arylboronic acid $R^2$—$B(OH)_2$, aryltin species $R^2$—$SnBu_3$ or an arylzinc species $R^2$—ZnCl. Such reagent types are well known in the art as, are the reaction conditions, catalysts, co-reagents, solvents, etc. Particularly preferred are those reactions where (II) and $R^2$—Y are coupled using a palladium or other suitable transition metal coupling reaction.

This type of reaction is exemplified in Preparation 6. Compounds of formula (II) may be made via conventional methods as exemplified in Preparation 5.

Where E is a suitable oxygen-protecting group such as ($C_{1-4}$ alkyl)CO, the protecting group may be removed during the reaction of method 1, using appropriate conditions, or subsequently, as discussed below.

Method 2

Compounds of formula (I) where $R^3$ is hydrogen may be made via hydrolysis of the corresponding ester of formula (III):

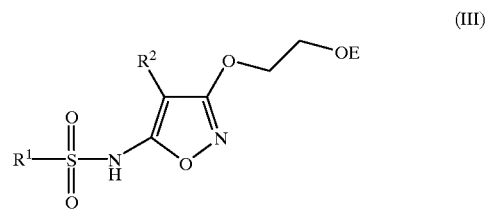

(III)

wherein E is ($C_{1-4}$ alkyl)CO, for example by treatment with aqueous base such as aqueous sodium hydroxide or aqueous potassium carbonate, in a suitable solvent such as methanol or ethanol.

Compounds of formula (III) may be made by the process of method 1, wherein E is ($C_{1-4}$ alkyl)CO, and is not removed during method 1.

Method 3

Compounds of formula (I) where $R^3$ is $aryl^1$ or $het^1$ can be made from the corresponding compound of formula (I) where $R^3$ is H, for instance via reaction of the compound of formula (I) where $R^3$ is H with a reagent of formula "$R^3$—$L^2$", where "$L^2$" is a suitable leaving group such as a halo, arenesulphonate, $C_{1-4}$ alkanesulphonate or perfluoro ($C_{1-4}$ alkane)sulphonate ion, suitably a chloride, phenylsulphonate, p-toluenesulphonate or mesylate ion, suitably in the presence of a base such as sodium hydride or potassium carbonate, in a suitable inert organic solvent such as N,N-dimethylformamide (DMF) or tetrahydrofuran (THF). Reagents of the formula "$R^3$—$L^2$" are well known in the art as, are the reaction conditions, catalysts, co-reagents, solvents, etc.

Preferably, R3 is 5-chloro-pyrimidin-2-yl or 5-bromo-pyrimidin-2-yl.

Compounds of formula (I) where $R^3$ is H, may be made via conventional methods as exemplified in Preparation 6.

This type of reaction is mentioned in for example U.S. Pat. No. 5,728,706 and *Tetrahedron* (1984) 40, 1433, and is exemplified below in Examples 2, 3 & 4.

Where desired or necessary the compound of formula (I) is converted into a pharmaceutically acceptable salt thereof. A pharmaceutically acceptable salt of a compound of formula (I) may be conveniently be prepared by mixing together solutions of a compound of formula (I) and the desired acid or base, as appropriate. The salt may be precipitated from solution and collected by filtration, or may be collected by other means such as by evaporation of the solvent, or by other means known to a man skilled in the art.

The compounds of the invention may be separated and purified by conventional methods.

The compounds of the present invention may be isolated and used per se or in the form of their pharmaceutically acceptable salts, solvates and/or hydrates. The term "salts" refers to inorganic and organic salts of a compound of the present invention. These salts can be prepared in situ during the final isolation and purification of a compound, or by separately reacting the compound or prodrug with a suitable organic or inorganic acid and isolating the salt thus formed. Representative salts include the hydrobromide, hydrochloride, sulfate, bisulfate, nitrate, acetate, oxalate, besylate, palmitiate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, Berge, et al., *J. Pharm. Sci.*, 66, 1–19 (1977).

The term "prodrug" means a compound that is transformed in vivo to yield a compound of Formula (I) or a pharmaceutically acceptable salt, hydrate or solvate of the compound. The transformation may occur by various mechanisms, such as through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

The invention also provides a compound of formula (I) or a pharmaceutically acceptable derivative thereof for use as a medicament.

The invention also provides for the use of a compound of formula (I) or pharmaceutically acceptable derivative thereof as defined above, in the manufacture of a medicament for the treatment of a condition mediated by endothelin, particularly endothelin $ET_A$.

The invention also provides for the use of a compound of formula (I) or pharmaceutically acceptable derivative thereof as defined above, in the manufacture of a medicament for the treatment of restenosis, acute/chronic renal failure, pulmonary hypertension, systemic hypertension; benign prostatic hyperplasia, male erectile dysfunction, prostate cancer, metastatic bone cancer, congestive heart failure, stroke, subarachnoid haemorrhage, angina, atherosclerosis, cerebral and cardiac ischaemia, prevention of ischaemia/reperfusion injury (e.g. allografts), cyclosporin induced nephrotoxicity, glaucoma, radiocontrast nephropathy, diabetic neuropathy, allergy, restoration of organ perfusion in haemorrhagic shock, lipoprotein lipase related disorders, chronic obstructive pulmonary disease and hyaline membrane disease in newborn.

The invention also provides a method of treating conditions mediated by endothelin, particularly $ET_A$, which comprises administering to a patient in need of such treatment a therapeutically effective amount of a compound of formula (I) or a pharmaceutically acceptable derivative thereof. The phrase "therapeutically effective amount" means an amount of a compound of the present invention that attenuates, ameliorates, or eliminates a particular disease, condition, or disorder, or prevents or delays the onset of a particular disease, condition, or disorder. The term "patient" refers to humans as well as other animal species such as companion animals (e.g., dogs, cats and horses), food-source animals (i.e., edible animals such as cows, pigs, sheep and poultry), zoo animals, and marine animals.

Particularly suitable conditions are selected from: restenosis, acute/chronic renal failure, pulmonary hypertension, systemic hypertension; benign prostatic hyperplasia, male erectile dysfunction, prostate cancer, metastatic bone cancer, congestive heart failure, stroke, subarachnoid haemorrhage, angina, atherosclerosis, cerebral and cardiac ischaemia, prevention of ischaemia/reperfusion injury (e.g. allografts), cyclosporin induced nephrotoxicity, glaucoma, radiocontrast nephropathy, diabetic neuropathy, allergy, restoration of organ perfusion in haemorrhagic shock, lipoprotein lipase related disorders, chronic obstructive pulmonary disease and hyaline membrane disease in newborn.

Reference to treatment herein includes prevention of undesirable conditions as well as alleviation or cure of said conditions.

The biological activity of the substances of the invention may be demonstrated as follows:

Dog Binding Assay

Competition between test substances and ligands binding to canine endothelin receptors is determined as follows:

Dog $ET_A$ Binding Assay

50 μl of a 500 pM solution of $^{125}$I-PD-151242 (Specific activity 2,000 Ci/mM) is mixed with 50 μl samples of test substances (final concentrations in the range from 0.01–10,000 nM). 100 μg of purified dog kidney homogenate is added in 150 μl of the following buffer: 50 mM Tris, 10 mM $MgCl_2$ and 0.05% Bovine Serum Albumen at pH 7.4. The solution is incubated at room temperature for 2 hours. After the incubation, the unbound ligand is separated from receptor bound ligand by filtration with a Brandel cell harvester, followed by 5 washes with buffer (Tris 50 mM, $MgCl_2$ 10 mM). Filter papers are counted for radioactivity and the $K_i$ (an $IC_{50}$ corrected for the dissociation constant and concentration of the ligand added) is determined for the concentration range tested.

Dog $ET_B$ Binding Assay

50 μl of a 100 pM solution of $^{125}$I-RL-1620 (Specific activity 2,200 Ci/mM) is mixed with 50 μl samples of test substances (final concentrations in the range from 0.01–10,000 nM). 50µg of purified Dog cerebellum homogenate is added in 150 µl of the following buffer; 50 mM Tris, 10 mM MgCl$_2$ and 0.05% Bovine Serum Albumen at pH 7.4. The solution is incubated at 30° C. for 90 minutes. After the incubation, the unbound ligand is separated from receptor bound ligand by filtration with a Brandel cell harvester, followed by 5 washes with buffer (Tris 50 mM, MgCl$_2$ 10 mM). Filter papers are counted for radioactivity and the K$_i$ (an IC$_{50}$ corrected for the dissociation constant and concentration of the ligand added) is determined for the concentration range tested.

The compounds of the present invention were investigated using the above assay and demonstrated strong ET$_A$ affinity and a marked selectivity for the ET$_A$ over the ET$_B$ receptor.

The compounds of the present invention can be administered alone but will generally be administered in admixture with a pharmaceutical carrier selected with regard to the intended route of administration and standard pharmaceutical or veterinary practice. For example they can be administered orally in the form of tablets containing such excipients as starch or lactose or in capsules or ovules either alone or in admixture with excipients or in the form of elixirs, solutions or suspensions containing the compound in a liquid carrier, for example a vegetable oil, glycerine or water with a flavoring or coloring agent. They can be injected parenterally, for example intravenously, intramuscularly or subcutaneously. For parental administration, they are best used as sterile aqueous solutions which may contain other substances, for example, enough glucose or salts to make the solution isotonic with blood. For parenteral administration, the compound of the present invention may also be administered as a solution or suspension in a suitable oil, for example polyethylene glycol, lecithin or sesame oil.

Compounds of the present invention may also be administered through inhalation of a solution, suspension or emulsion that may be administered as a dry powder or in the form of an aerosol using a conventional propellant such as dichlorodifluoromethane.

For oral or parenteral administration to human patients, the daily dosage levels of the compounds of the present invention will be from about 0.01 to about 30 mg/kg (in single or divided doses) and preferably will be in the range about 0.01 to about 5 mg/kg. Thus tablets will contain about 1 mg to about 0.4 g of substance for administration singly or two or more at a time, as appropriate. The above dosages are, of course only exemplary of the average case and there may be instances where higher or lower doses are merited, and such are within the scope of the present invention.

Alternatively the compounds of the present invention can be administered in the form of a suppository or pessary, or they may be applied topically in the form of a lotion, solution, cream, ointment or dusting powder or in the form of a medicated plaster, patch or membrane. For example they may be incorporated in a cream containing an aqueous emulsion of polyethylene glycols or liquid paraffin. The compounds may also be administered intranasally.

For veterinary use, although it is possible to administer a compound of the present invention directly without any formulation, the compounds are preferably employed in the form of a pharmaceutical or veterinary formulation comprising a pharmaceutically or veterinarily acceptable carrier, diluent or excipient and a compound of the present invention. Such compositions will contain from about 0.1 percent by weight to about 90.0 percent by weight of the active ingredient.

The methods by which the inventive compounds may be administered include oral administration by capsule, bolus, tablet or drench, topical administration as an ointment, a pour-on, spot-on, dip, spray, mousse, shampoo or powder formulation or, alternatively, they can be administered by injection (e.g. subcutaneously, intramuscularly or intravenously), or as an implant.

Such formulations are prepared in a conventional manner in accordance with standard veterinary practice. Thus capsules, boluses or tablets may be prepared by mixing the active ingredient (i.e., inventive compound) with a suitable finely divided diluent or carrier additionally containing a disintegrating agent and/or binder such as starch, lactose, talc or magnesium stearate, etc. Oral drenches are prepared by dissolving or suspending the active ingredient in a suitable medium. Pour-on or spot-on formulations may be prepared by dissolving the active ingredient in an acceptable liquid carrier vehicle such as butyl digol, liquid paraffin or a non-volatile ester, optionally with the addition of a volatile component such as propan-2-ol.

Alternatively, pour-on, spot-on or spray formulations can be prepared by encapsulation, to leave a residue of active agent on the surface of the animal. Injectable formulations may be prepared in the form of a sterile solution which may contain other substances, for example enough salts or glucose to make the solution isotonic with blood. Acceptable liquid carriers include vegetable oils such as sesame oil, glycerides such as triacetin, esters such as benzyl benzoate, isopropyl myristrate and fatty acid derivatives of propylene glycol, as well as organic solvents such as pyrrolidin-2-one and glycerol formal. The formulations are prepared by dissolving or suspending the active ingredient in the liquid carrier such that the final formulation contains from about 0.1 to about 10% by weight of the active ingredient.

These formulations will vary with regard to the weight of active ingredient contained therein, depending on the species of animal to be treated, the severity and type of infection and the body weight of the animal. For parenteral, topical and oral administration, typical dose ranges of the active ingredient are about 0.01 to about 100 mg per kg of body weight of the animal. Preferably the range is about 0.1 to about 10 mg per kg.

The compositions are preferably formulated in a unit dosage form, each dosage containing from about 1 to about 500 mg, more usually about 5 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

As an alternative for veterinary use the substances may be administered with animal feedstuff and for this purpose a concentrated feed additive or premix may be prepared for mixing with the normal animal feed.

Thus, according to a further aspect of the present invention, there are provided pharmaceutical formulations comprising a compound of the present invention, as defined above, and a pharmaceutically-acceptable adjuvant, diluent or carrier.

High performance liquid chromatography (HPLC) retention times and UV spectra were recorded using a Hewlett-Packard™ 1090 LUSI diode-array spectrophotometer (method A). All NMR spectra were measured in CDCl$_3$ or MeOD by an Inova™ 300 MHz or 400 MHz spectrometer unless otherwise indicated and peak positions are expressed in parts per million (ppm) downfield from tetramethylsilane. The peak shapes are denoted as follows: s, singlet; d, doublet; t, triplet; q, quartet; m, multiplet; br broad. High resolution MS data was acquired on a AutoSpecQ with electrospray ionization (ESI) or thermospray ionization (TSPI) using a PEG reference (or on a Brüker Apex II FTMS with ESI where indicated).

| MY Inoculum and Production Medium | |
|---|---|
| Glucose | 10 g |
| Peptone (Difco ™) | 5 g |
| Yeast extract (Oxoid ™) | 3 g |
| Malt extract (Oxoid ™) | 5 g |
| Tap water | 1 L |
| NaOH | To a pH 6.3–6.5 |

EXAMPLE 1

N-(4-(1.3-benzodioxol-5-yl)-3-{2-[(5-bromo-2-pyrimidinyl)oxyl]ethoxy}-5-isoxazolyl)-(2-hydroxy-1,1-dimethylethyl)benzenesulfonamide

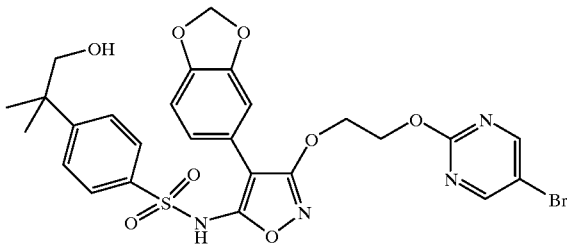

*Amycolata autotrophica* ATCC35203 maintained on a quarter strength ATCC172 agar slope was inoculated as a loopful of spores into a 300 ml Erlenmeyer flasks each containing 50 ml of MY inoculum medium. This was allowed to incubate for 2 days at 28° C., 200 rpm on an Infors Multitron™ Shaker with 1 ″ throw. Two mLs of this inoculum was then transferred to each of twenty 300 ml Erlenmeyer flask containing 50 ml of MY production medium and incubated under the same conditions for a further 24 hours. At this point 5 mg of N-(4-(1,3-benzodioxol-5-yl)-3-{2-[(5-bromo-2-pyrimidinyl)oxy]ethoxy}-5-isoxazolyl)-4-(tert-butyl)benzene-sulfonamide (Example 2) dissolved in 0.5 mL of methanol was added to each of the flasks and the fermentation allowed to continue under the same conditions for a further 144 hours. Each flask was then extracted with 200 mls of ethyl acetate and the combined ethyl acetate solubles concentrated to dryness to give a gum solid.

The crude extract was purified by preparative reversed phase HPLC with a Phenomenex Magellen™ 5 µ C18 column (150 mm×21.2 mm) in two injections. Using a gradient mobile phase of 35:65 to 20:80 water/methanol from 1.5 to 29 minutes at a flow rate of 20 mL/min, the product was eluted at 4.1 minutes. The product fractions were purified again on the same column in one injection. Using a gradient mobile phase of 85% to 15% water/methanol from 0 to 25 minutes at a flow rate of 20 mL/min, the product was eluted at 14.9 minutes. The product fractions were concentrated under reduced pressure to yield the title compound as a colorless amorphous solid (2.0 mg).

δH (300 MHz, CDCI$_3$) 8.40 (2H, s), 7.70 (2H, d), 7.10 (2H, d), 7.05 (2H, m), 6.55 (1H, d), 5.75 (2H, s), 4.55 (2H, m), 4.40 (2H, m), 3.35 (2H, s), 1.05 (6H, s) m/z (ESI) [M+H]$^+$=633.0655, $C_{26}H_{26}{}^{79}BrN_4O_8S$ requires 633.0655 m/z (ESI) [M+Na]$^+$=655.0481, $C_{26}H_{25}{}^{79}BrN_4O_8SNa$ requires 655.0474

EXAMPLE 2

N-(4-(1,3-benzodioxol-5-yl)-3-{2-[(5-bromo-2-pyrimidinyl)oxy]ethoxyl}-5-isoxazolyl)-4-(tert-butyl)benzenesulfonamide

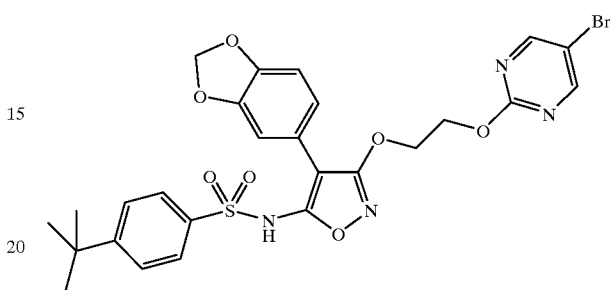

To a solution of N-[4-(1,3-benzodioxol-5-yl)-3-(2-hydroxyethoxy)-5-isoxazolyl]-4-(tert-butyl)benzenesulfonamide (Preparation 6) (90 mg) in tetrahydrofuran (1.5 mL), purged with nitrogen three times, was added sodium hydride (16 mg of a 60% dispersion in oil) and the reaction mixture stirred for 15 minutes. After which time a solution of 5-bromo-2-chloropyrimidine (41 mg) in tetrahydrofuran (0.5 mL) was added to the reaction followed by dimethylacetamide (0.1 mL). The reaction mixture was left stirring at room temperature overnight. This solution was added to a stirring mixture of ether (30 mL) and citric acid (1.0 M, 30 mL) The organics were separated and further washed with brine (30 ml) and dried over magnesium sulfate before being concentrated in-vacuo to yield the crude material (90 mg). This was purified by HPLC on a 5 µ ODS Phenomenex Magellen™ column with an isocratic elution of 0.1 M NH$_4$OAc (55%) and acetonitrile (45%) to yield the desired product as a white solid (10 mg).

δH (300 MHz, CDCI$_3$) 8.50(2H, s), 7.85(2H, d), 7.50(2H, d), 6.85(2H, d), 6.75(1H, d), 5.95(2H, s), 4.75(2H, m), 4.65(2H, m), 1.35(9H, s) m/z (thermospray) [MH$^+$]=617.5, $C_{26}H_{26}BrN_4O_7S$ requires 617.5.

EXAMPLE 3

N-(4-(1,3-benzodioxol-5-yl)-3-{2-[5-chloro-2-pyrimidinyl)oxy]ethoxy}-5-isoxazolyl)-4-(tert-butyl)benzenesulfonamide

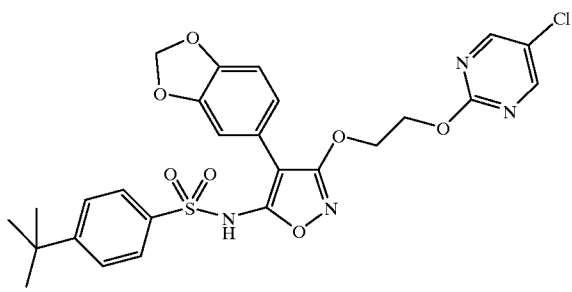

To a solution of N-[4-(1,3-benzodioxol-5-yl)-3-(2-hydroxyethoxy)-5-isoxazolyl]-4-(tert-butyl)

benzenesulfonamide (Preparation 6) (104 mg) in tetrahydrofuran (3 mL), purged with nitrogen three times, was added sodium hydride (19 mg of a 60% dispersion in oil) and the reaction mixture stirred for 15 minutes. After which time a solution of 5-chloro-2-(methylsulfonyl)pyrimidine (48 mg) in dimethylformamide (0.5 mL) was added to the reaction mixture and then left stirring at room temperature overnight. The reaction mixture was quenched with citric acid (1.0 M, 20 mL) and extracted into ethyl acetate (30 mL). The organics were washed with water (20 mL), brine (20 ml) and dried over magnesium sulfate before being concentrated in vacuo to yield the crude material (45 mg). This was purified by HPLC on a 5 μ ODS Phenomenex Magellen™ column with a gradient elution of 0.1 M NH₄OAc (95% to 55%) and acetonitrile (5% to 45%) to yield the desired product as a white solid (25 mg).

δH (300 MHz, CDCl₃): 8.40(2H, s), 7.80(2H, d), 7.45 (2H, d), 6.85(2H, d), 6.70(1H, d), 5.95(2H, s), 4.70(2H, m), 4.60(2H, m), 1.35(9H, s) 6.75(1H, d), 5.95(2H, s), 4.75(2H, m), 4.65(2H, m), 1.35(9H, s) m/z (thermospray) [MH⁺]= 573.1, $C_{26}H_{26}IN_4O_7S$ requires 573.0.

EXAMPLE 4

N-[4-(1,3-benzodioxol-5-yl)-3-(2-{[5-(methylsulfanyl)-2-pyrimidinyl] oxy}ethoxy)-5-isoxazolyl]-4-(tert-butyl)benzenesulfonamide

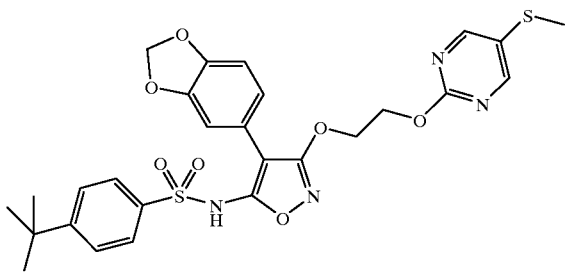

To a solution of N-[4-(1,3-benzodioxol-5-yl)-3-(2-hydroxyethoxy)-5-isoxazolyl]-4-(tert-butyl) benzenesulfonamide (Preparation 6) (109 mg) in tetrahydrofuran (3 mL), purged with nitrogen three times, was added sodium hydride (20 mg of a 60% dispersion in oil) and the reaction mixture stirred for 15 minutes. After which time a solution of 2-chloro-5-(methylsulfanyl)pyrimidine (42 mg) in dimethylformamide (0.5 mL) was added to the reaction mixture and then left stirring at room temperature overnight. The reaction mixture was quenched with citric acid (1.0 M, 10 mL) and extracted into ethyl acetate (15 mL). The organics were washed with water (10 mL), brine (10 mL) and dried over magnesium sulfate before being concentrated in vacuo to yield the crude material (150 mg). This was purified by HPLC on a 5 μ ODS Phenomenex Magellen™ column with a gradient elution of 0.1 M NH₄OAc (95% to 50%) and acetonitrile (5% to 50%) to yield the desired product as a white solid (16 mg).

δH (300 MHz, CDCl₃): 8.50(2H, s), 7.80(2H, d), 7.60 (1H, br), 7.50(2H, d), 6.80(2H, d), 6.65(1H, d), 5.95(2H, s), 4.70(2H, m), 4.60(2H, m), 2.45(3H, s), 1.35(9H, s) m/z (thermospray) [MH⁺]=584.7, $C_{27}H_{29}N_4O_7S_2$ requires 584.7.

EXAMPLE 5

N-[4-(1,3-benzodioxol-5-yl)-3-(2-{[5-(methylsulfonyl)-2-pyrimidinyl] oxy}ethoxy)-5-isoxazolyl]-4-(tert-butyl)benzenesulfonamide

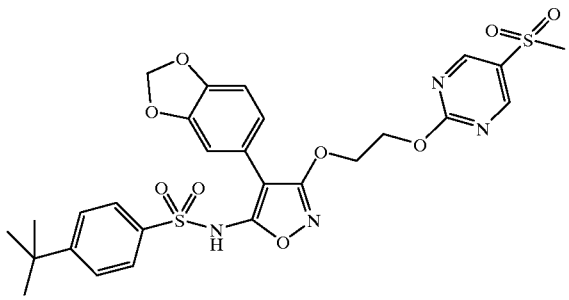

To a suspension of N-[4-(1,3-benzodioxol-5-yl)-3-(2-{[5-(methyl sulfanyl)-2-pyrimidinyl] oxy}ethoxy)-5-isoxazolyl]-4-(tert-butyl) benzenesulfonamide (Example 4) (15 mg) in dichloromethane (0.3 mL) was added m-chloroperoxybenzoic acid (7 mg) in dichloromethane (0.2 mL). The reaction mixture was left stirring at room temperature overnight. The solvent was removed in vacuo to yield the crude material as an orange solid (20 mg). This was purified by HPLC on a 5μ ODS Phenomenex Magellen™ column with a gradient elution of 0.1 M NH₄OAc (95% to 60%) and acetonitrile (5% to 40%) to yield the desired product as a white solid (6 mg). δH (300 MHz, CDCl₃): 8.95(2H, s), 7.80(2H, d), 7.50(2H, d), 7.10(1H, br), 6.80(2H, d). 6.70(1H, d), 5.95(2H, s), 4.90(2H, m), 4.70(2H, m), 3.15(3H, s), 1.35(9H, s) m/z (thermospray) [MH⁺]=616.6, $C_{27}H_{29}N_4O_9S_2$ requires 616.7

Preparation 1

Tert-Butyl 3-[2-(acetox)ethoxy]-5-amino-4-isoxazolecarboxylate

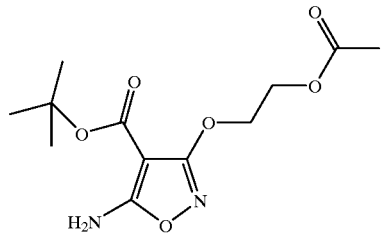

To a stirring solution of tert-butyl 5-amino-3-(2-hydroxyethoxy)-4-isoxazolecarboxylate (R. Neidlein, *J. Heterocyclic Chem.*, 1989, 26, 1335) (5.60 g) and triethylamine (3.36 ml) in tetrahydrofuran (50 mL) at room temperature was added 4-dimethylaminopyridine (280 mg) followed by acetic anhydride (2.81 g). The reaction was stirred for 2 hours at room temperature. The solvent was removed in vacuo to yield the crude material (6.0 g). The crude material was purified using the Biotagem™ Flash 40i System (silica, 90 g), eluting with ethyl acetate:hexane (1:1) to yield the product as an off white solid (5.0 g)

δH (300 MHz, CDCl₃): 5.80 (2H, br), 4.40–4.45 (4H, m), 2.10 (3H, s), 1.55 (9H, s)

Preparation 2

Tert-Butyl-3-[(acetoxy)ethoxy]-5-({[4-(tert-butyl)phenyl]sulfonyl}amino)-4-isoxazolecarboxylate

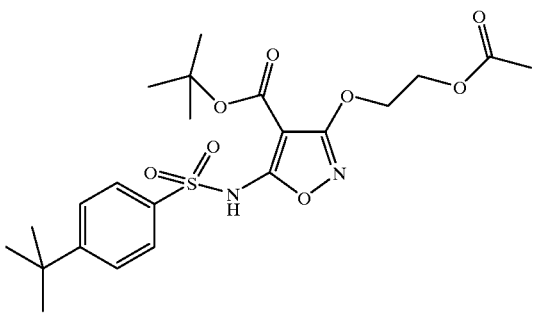

To a stirring solution of tert-butyl 3-[2-(acetoxy)ethoxy]-5-amino-4-isoxazolecarboxylate (Preparation 1) (6.0 g) in tetrahydrofuran (55 mL) under an atmosphere of nitrogen, was added sodium hydride (1.68 g of a 60% dispersion in oil). The reaction was stirred for 15 minutes after which time tert-butylbenzenesulfonyl chloride (5.14 g) was added. The reaction was stirred at room temperature overnight. The solvent was removed in vacuo and redissolved in dichloromethane (50 mL) and then washed with water (50 mL with 3 drops of HCl). The organics were further washed with brine (40 mL), dried over magnesium sulfate and concentrated under reduced pressure to yield the crude material (7.0 g). The crude material was purified using the Biotage™ Flash 40i system (silica, 90 g) with a gradient elution of ethyl acetate (10% to 95%) and dichloromethane (90% to 5%) to yield the desired product as a white solid (3.5 g).

δH (300 MHz, d$_6$DMSO): 7.75 (2H, d), 7.45 (2H, d), 4.15–4.30 (4H, m), 2.00 (3H, s), 1.40 (9H, s), 1.30 (9H, s)

Preparation 3

2-{[5-({[4-(tert-butyl)phenyl]sulfonyl}amino)-3-isoxazoly]oxy}ethyl Acetate

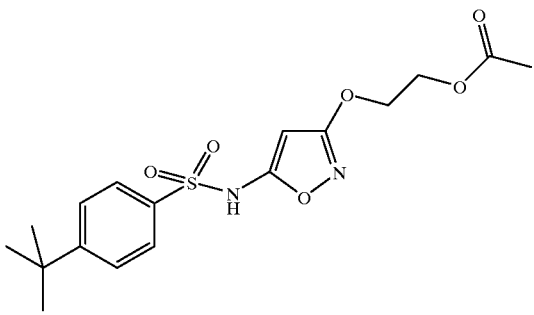

To a solution of tert-butyl 3-[2-(acetoxy)ethoxy]-5-({[4-(tert-butyl)phenyl]sulfonyl}amino)-4-isoxazolecarboxylate (Preparation 2) (3.16 g) in dichloromethane (40 mL) was added trifluoroacetic acid (20 mL). The reaction mixture was heated to reflux for 3 hours. After which time the reaction mixture was basified to pH8 using sodium hydrogen carbonate solution and then re-acidified to pH2 using aqueous hydrochloric acid (1.0 M). This aqueous layer was extracted into ethyl acetate (2×250 mL) and the organics combined, dried over magnesium sulfate and the solvent removed in vacuo to yield the crude material (2.6 g). This was dissolved up in toluene and refluxed for 2 hours. The solvent was removed in vacuo to yield the crude material as a light brown solid (2.3 g). The crude material was purified using the Biotage Flash 40i system (silica, 90 g) and eluted with hexane:ethyl acetate (5:2) to yield the product as a white solid (1.2 g).

δH (300 MHz, CDCl$_3$): 7.80 (2H, d), 7.55 (2H, d), 5.65 (1H, s), 4.35–4.40 (4H, m), 2.10 (3H, s), 1.35 (9H, s)

Preparation 4

2-{[5-({[4-(tert-butyl)phenyl]sulfony}amino)-4-iodo-3-isoxazolyl]oxy}ethyl Acetate

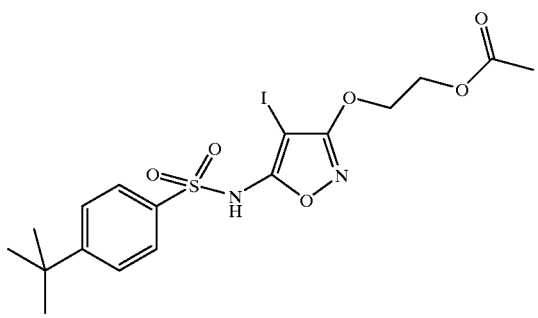

To a stirring solution of 2-{[5-({[4-(tert-butyl)phenyl]sulfonyl}amino)-3-isoxazolyl]oxy}ethyl acetate (Preparation 3) (1.17 g) in tetrahydrofuran (10 mL) was added N-iodosuccinimide (0.76 g). The reaction mixture was left stirring at room temperature overnight. The solvent was removed in vacuo to yield the crude material as a brown oil (1.5 g). The crude material was purified using the Biotage™ Flash 40i system (silica, 90 g) and eluted with hexane:ethyl acetate (1:9) to yield the product as a brown oil.

δH (300 MHz, CDCl$_3$): 7.90 (2H, d), 7.55 (2H, d), 4.35–4.45 (4H, m), 2.10 (3H, s), 1.35 (9H, s)

Preparation 5

2-({5-[{[4-(tert-butyl)phenyl]sulfonyl}(isobutoxycarbonyl) Amino]-4-iodo-3-isoxazolyl}oxy)ethyl Acetate

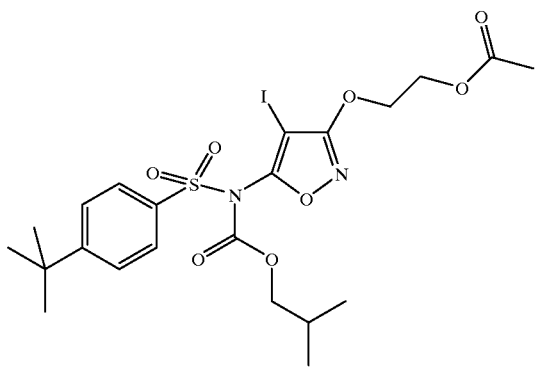

To a stirring solution of 2-{[5-({[4-(tert-butyl)phenyl]sulfonyl}amino)-4-iodo-3-isoxazolyl]oxy}ethyl acetate (Preparation 4) (9.44 g) in dichloromethane was added pyridine (1.65 mL) followed by the slow addition of isobutylchloroforomate (2.41 mL) over 10 minutes. The reaction mixture was stirred at room temperature for one hour. The solvent was removed in vacuo to yield the crude material. This was purified using column chromatography (300 g silica, compound loaded with dichloromethane (15 mL) using a gradient elution of hexane (100% to 75%) and ethyl acetate (0% to 25%) to yield the desired compound as a yellow oil (7.70 g).

δH (300 MHz, CDCl$_3$): 8.05 (2H, d), 7.60 (2H, d), 4.50 (2H, m), 4.45 (2H, m), 3.90 (2H, d), 2.15 (3H, s), 1.85 (1H, m), 1.35 (9H, s), 0.80 (6H, d)

Preparation 6

N-[4-(1,3-benzodioxol-5-yl)-3-(2-hydroxyethoxy)-5-isoxazolyl]-4-(tert-butyl)benzenesulfonamide

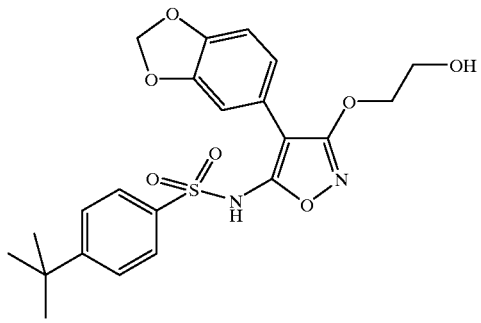

To a stirring solution of 2-({5-[{[4-(tert-butyl)phenyl]sulfonyl}(isobutoxycarbonyl)amino]-4-iodo-3-isoxazolyl}oxy)ethyl Acetate (Preparation 5) (2.41 g) in dioxane (25 mL) was added 3,4-methylenedioxybenzeneboronic acid (0.72 g) followed by cesium carbonate (5.15 g) and water (3 mL). The reaction mixture was purged with nitrogen three times, after which time tetrakis(triphenylphosphine)-palladium(O) (140 mg). The reaction mixture was heated to reflux for about 2 hours. Ethanol (50 mL) and sodium hydroxide (2M, 50 mL) were added to the reaction mixture and then this was stirred at room temperature overnight. The reaction mixture was concentrated in vacuo and the solid residue was partitioned between saturated ammonium chloride solution (100 mL) and ethyl acetate (100 mL). The organics were washed with brine (50 mL), dried over sodium, sulfate and concentrated under reduced pressure to yield the crude material as a brown oil. The crude material was purified by column chromatography (100 g silica) using a gradient elution of hexane (50% to 0%) and ethyl acetate (50% to 100%) and also with methanol (5% in ethyl acetate) to yield the product as a light brown foam (770 mg).

δH (300 MHz, d$_6$DMSO): 7.65 (2H, d), 7.50 (2H, d), 6.95 (1H, s), 6.90 (2H, d), 6.80 (2H, d), 6.00 (2H, s), 4.10 (2H, t), 3.70 (2H, t), 1.15 (9H, s)

What is claimed is:
1. A compound of formula (I)

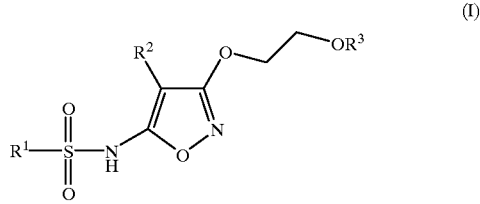

wherein
  $R^1$ is
  (a) a phenyl group,
  (b) a 5- or 6-membered heterocyclic group containing one to three heteroatoms each independently selected from the group consisting of N, O and S, said heterocyclic group being optionally fused to a benzo group,
  (c) CHR$^6$CHR$^7$Ph, or
  (d) CR$^6$=CR$^7$Ph,
    where groups (a), (b), (c) and (d) are optionally each independently substituted with one to three substituents selected from the group consisting of halo, C$_{1-6}$ alkyl optionally substituted by OH, halogen, NR$^4$R$^5$, OCOR$^4$, CO$_2$R$^4$, CN, O(C$_{1-6}$ alkyl optionally substituted by one or more halogens), and CO$_2$R$^4$, where R$^4$ and R$^5$ are each independently H or C$_{1-6}$ alkyl optionally substituted by one or more halo, and R$^6$ and R$^7$ are each independently H or C$^{1-3}$ alkyl;
  $R^2$ is aryl$^1$ or het$^1$; and
  $R^3$ is H, C$_{1-6}$ alkyl, C(O)R$^4$, CONHaryl$^1$, CONHhet$^1$, aryl$^1$ and het$^1$;
    where aryl$^1$ is a phenyl or a naphthyl group, said phenyl and said naphthyl groups being optionally substituted with one to three substituents each independently selected from the group consisting of C$_{1-3}$ alkyl, CF$_3$, halo, C$_{1-3}$ alkoxy, OCF$_3$, OH, NO$_2$, CN, NR$^4$R$^5$, COR$^4$, CO$_2$R$^4$, CONR$^4$R$^5$, S(O)$_p$(C$_{1-3}$ alkyl), CH$_2$NR$^4$R$^5$, NR$^4$COR$^5$, COCF$_3$, CH$_2$OH, S(O)$_p$CF$_3$, C(=NH)NH$_2$, C$_{2-3}$ alkynyl, C$_{2-3}$ alkenyl, phenyl and het$^2$,
  het$^1$ is a 5- to 7-membered fully saturated, partially unsaturated, or fully unsaturated heterocyclic group containing one to three hetero-atoms each independently selected from the group consisting N, O and S, said heterocyclic group being optionally fused to a benzo group and optionally substituted with one to three substituents each independently selected from the group consisting of C$_{1-3}$ alkyl, CF$_3$, halo, C$_{1-3}$ alkoxy, (C$_{1-5}$ alkyl)OH, (C$_{1-5}$ alkyl)CO$_2$H, CF$_3$O, OH, NO$_2$, CN, NR$^4$R$^5$, COR$^4$, CO$_2$R$^4$, CONR$^4$R$^5$, S(O)$_p$(C$_{1-3}$ alkyl), CH$_2$NR$^4$R$^5$, NR$^4$COR$^5$, COCF$_3$, CH$_2$OH, S(O)$_p$CF$_3$, C(=NH)NH$_2$, C$_{2-3}$ alkynyl, C$_{2-3}$ alkenyl, phenyl and het$^2$, with the proviso that when R$^3$ is het$^1$, the het$^1$ group is linked to the adjacent O atom by a carbon atom,
  het$^2$ is a 5- to 7-membered fully saturated, partially unsaturated, or fully unsaturated heterocyclic group containing one to three hetero-atoms each independently selected from the group consisting of N, O and S,
  and p is 0, 1 or 2;
or a pharmaceutically acceptable derivative thereof.

2. The compound of claim 1 wherein $R^1$ is a phenyl group or a 5- or 6-membered heterocyclic group containing one to three heteroatoms each independently selected from the group consisting of O, S and N, said phenyl and said heterocyclic groups being optionally substituted by 1 to 3 substituents each independently selected from the group consisting of halo and $C_{1-6}$ alkyl optionally substituted by OH or $CO_2H$; or a pharmaceutically acceptable derivative thereof.

3. The compound of claim 2 wherein $R^1$ is a phenyl group optionally substituted by $C_{1-6}$ alkyl, where said $C_{1-6}$ alkyl is optionally substituted by OH or $CO_2H$; or a pharmaceutically acceptable derivative thereof.

4. The compound of claim 3 wherein $R^1$ is a phenyl substituted at the 4 position by t-butyl or 2-hydroxy-1,1-dimethylethyl; or a pharmaceutically acceptable derivative thereof.

5. The compound of claim 1 wherein $R^2$ is a phenyl group or a 5- to 7-membered heterocyclic group containing one to three heteroatoms each independently selected from the group consisting of O, S and N, where said heterocyclic group is optionally fused to a benzo group, and said phenyl and said heterocyclic groups are optionally substituted by 1 to 3 substituents selected from the group consisting of halogen and $C_{1-6}$ alkyl optionally substituted by OH or $CO_2H$; or a pharmaceutically acceptable derivative thereof.

6. The compound of claim 5 wherein $R^2$ is benzodioxol or 4-methylphenyl; or a pharmaceutically acceptable derivative thereof.

7. The compound of claim 6 wherein $R^2$ is a 1,3-benzodiox-5-ol; or a pharmaceutically acceptable derivative thereof.

8. The compound of claim 1 wherein $R^3$ is selected from the group consisting of
   i) hydrogen,
   ii) $C_{1-6}$ alkyl,
   iii) $C(O)C_{1-6}$ alkyl,
   iv) phenyl, and
   v) 5- to 7-membered heterocyclic group containing one to three heteroatoms each independently selected from the group consisting of O, S and N,
where said heterocyclic group is optionally fused to a benzo group, and said phenyl and said heterocyclic groups are optionally substituted with halo, $(C_{1-5}$ alkyl)OH, $(C_{1-5}$ alkyl)$CO_2H$, or $SO_pR^4$, where p is 0, 1 or 2; or a pharmaceutically acceptable derivatives thereof.

9. The compound of claim 8 wherein $R^3$ is hydrogen, $C(O)CH_3$, or pyrimidine optionally substituted by chloro, bromo, $(C_{1-5}$ alkyl)OH, $(C_{1-5}$ alkyl)$CO_2H$, or $SO_pCH_3$, where p is 0, 1 or 2; or a pharmaceutically acceptable derivatives thereof.

10. The compound of claim 9 wherein $R^3$ is 4-chloropyrimidinyl; or a pharmaceutically acceptable derivative thereof.

11. The compound of claim 1 wherein $R^4$ and $R^5$ are hydrogen or $C_{1-6}$ alkyl; or a pharmaceutically acceptable derivative thereof.

12. The compound of claim 11 wherein $R^4$ and $R^5$ are hydrogen or $C_{1-3}$ alkyl; or a pharmaceutically acceptable derivative thereof.

13. The compound of claim 12 wherein $R^4$ and $R^5$ are $CH_3$; or a pharmaceutically acceptable derivative thereof.

14. The compound of claim 1 wherein $R^6$ and $R^7$ are hydrogen or $CH_3$; or a pharmaceutically acceptable derivative thereof.

15. The compound of claim 14 wherein $R^6$ and $R^7$ are hydrogen; or a pharmaceutically acceptable derivative thereof.

16. The compound of claim 1 wherein said compound is selected from the group consisting of
   N-(4-(1,3-benzodioxol-5-yl)-3-{2-[(5-chloro-2-pyrimidinyl) oxy]ethoxy}-5-isoxazolyl)-4-(tert-butyl)benzenesulfonamide;
   N-(4-(1,3-benzodioxol-5-yl)-3-{2-[(5-bromo-2-pyrimidinyl) oxy]ethoxy}-5-isoxazolyl)-4-(tett-butyl)benzenesulfonamide; and
   N-(4-(1,3-benzodioxol-5-yl)-3-{2-[(5-bromo-2-pyrimidinyl)oxy]ethoxy}-5-isoxazolyl)-4-(2-hydroxy-1,1-dimethylethyl)benzenesulfonamide; or
a pharmaceutically acceptable derivative thereof.

17. A pharmaceutical composition comprising
(a) a compound of formula (I)

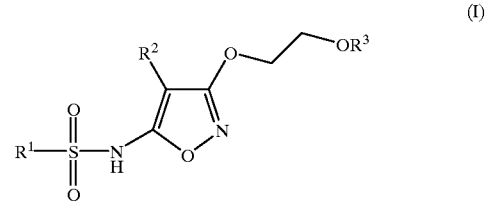

wherein
$R^1$ is
   (a) a phenyl group,
   (b) a 5- or 6-membered heterocyclic group containing one to three heteroatoms each independently selected from the group consisting of N, O and S, said heterocyclic group being optionally fused to a benzo group,
   (c) $CHR^6CHR^7Ph$, or
   (d) $CR^6=CR^7Ph$,
      where groups (a), (b), (c) and (d) are optionally each independently substituted with one to three substituents selected from the group consisting of halo, $C_{1-6}$ alkyl optionally substituted by OH, halogen, $NR^4R^5$, $OCOR^4$, $CO_2R^4$, CN, $O(C_{1-6}$ alkyl optionally substituted by one or more halogens), and $CO_2R^4$, where $R^4$ and $R^5$ are each independently H or $C_{1-6}$ alkyl optionally substituted by one or more halo, and $R^6$ and $R^7$ are each independently H or $C_{1-3}$ alkyl;
$R^2$ is aryl$^1$ or het$^1$; and
$R^3$ is H, $C_{1-6}$ alkyl, $C(O)R^4$, $CONHaryl^1$, $CONHhet^1$, aryl$^1$ and het$^1$;
   where aryl$^1$ is a phenyl or a naphthyl group, said phenyl and said naphthyl groups being optionally substituted with one to three substituents each independently selected from the group consisting of $C_{1-3}$ alkyl, $CF_3$, halo, $C_{1-3}$ alkoxy, $OCF_3$, OH, $NO_2$, CN, $NR^4R^5$, $COR^4$, $CO_2R^4$, $CONR^4R^5$, $S(O)_p(C_{1-3}$ alkyl), $CH_2NR^4R^5$, $NR^4COR^5$, $COCF_3$, $CH_2OH$, $S(O)_pCF_3$, $C(=NH)NH_2$, $C_{2-3}$ alkynyl, $C_{2-3}$ alkenyl, phenyl and het$^2$;
   het$^1$ is a 5- to 7-membered fully saturated, partially unsaturated, or fully unsaturated heterocyclic group containing one to three hetero-atoms each independently selected from the group consisting N, O and S, said heterocyclic group being optionally fused to a benzo group and optionally substituted with one to three substituents each independently selected from the group consisting of $C_{1-3}$ alkyl, $CF_3$, halo, $C_{1-3}$ alkoxy, $(C_{1-5}$ alkyl)OH, ($C_{1-5}$ alkyl)$CO_2H$, $CF_3O$, $OH$, $NO_2$, $CN$, $NR^4R^5$, $COR^4$, $CO_2R^4$, $CONR^4R^5$, $S(O)_p(C_{1-3}$ alkyl), $CH_2NR^4R^5$, $NR^4COR^5$, $COCF_3$, $CH_2OH$, $S(O)_p CF_3$, $C(=NH)NH_2$, $C_{2-3}$ alkynyl, $C_{2-3}$ alkenyl, phenyl and het$^2$, with the proviso that when $R^3$ is het$^1$, the het$^1$ group is linked to the adjacent O atom by a carbon atom, het$^2$ is a 5- to 7-membered fully saturated, partially unsaturated, or fully unsaturated heterocyclic group containing one to three hetero-atoms each independently selected from the group consisting of N, O and S, and p is 0, 1 or 2;

or a pharmaceutically acceptable derivative thereof; and (b) a pharmaceutically-acceptable adjuvant, diluent or carrier.

18. The pharmaceutical composition of claim 17 wherein $R^1$ is a phenyl group or a 5- or 6-membered heterocyclic group containing one to three heteroatoms each independently selected from the group consisting of O, S and N, said phenyl and said heterocyclic groups being optionally substituted by 1 to 3 substituents each independently selected from the group consisting of halo and $C_{1-6}$ alkyl optionally substituted by OH or $CO_2H$; or a pharmaceutically acceptable derivative thereof.

19. The pharmaceutical composition of claim 18 wherein $R^1$ is a phenyl group optionally substituted by $C_{1-6}$ alkyl, where said $C_{1-6}$ alkyl is optionally substituted by OH or $CO_2H$; or a pharmaceutically acceptable derivative thereof.

20. The pharmaceutical composition of claim 19 wherein $R^1$ is a phenyl substituted at the 4 position by t-butyl or 2-hydroxy-1,1-dimethylethyl; or a pharmaceutically acceptable derivative thereof.

21. The pharmaceutical composition of claim 17 wherein $R^2$ is a phenyl group or a 5- to 7-membered heterocyclic group containing one to three heteroatoms each independently selected from the group consisting of O, S and N, where said heterocyclic group is optionally fused to a benzo group, and said phenyl and said heterocyclic groups are optionally substituted by 1 to 3 substituents selected from the group consisting of halogen and $C_{1-6}$ alkyl optionally substituted by OH or $CO_2H$; or a pharmaceutically acceptable derivative thereof.

22. The pharmaceutical composition of claim 21 wherein $R^2$ is benzodioxol or 4-methylphenyl; or a pharmaceutically acceptable derivative thereof.

23. The pharmaceutical composition of claim 22 wherein $R^2$ is a 1,3-benzodiox-5-ol; or a pharmaceutically acceptable derivative thereof.

24. The pharmaceutical composition of claim 17 wherein $R^3$ is selected from the group consisting of i) hydrogen, ii) $C_{1-6}$ alkyl, iii) $C(O)C_{1-6}$ alkyl, iv) phenyl, and vi) 5- to 7-membered heterocyclic group containing one to three heteroatoms each independently selected from the group consisting of O, S and N, where said heterocyclic group is optionally fused to a benzo group, and said phenyl and said heterocyclic groups are optionally substituted with halo, ($C_{1-5}$ alkyl)OH, ($C_{1-5}$ alkyl)$CO_2H$, or $SO_pR^4$, where p is 0, 1 or 2; or a pharmaceutically acceptable derivatives thereof.

25. The pharmaceutical composition of claim 24 wherein $R^3$ is hydrogen, $C(O)CH_3$, or pyrimidine optionally substituted by chloro, bromo, ($C_{1-5}$ alkyl)OH, ($C_{1-5}$ alkyl)$CO_2H$, or $SO_pCH_3$, where p is 0, 1 or 2; or a pharmaceutically acceptable derivatives thereof.

26. The pharmaceutical composition of claim 25 wherein $R^3$ is 4-chloropyrimidinyl; or a pharmaceutically acceptable derivative thereof.

27. The pharmaceutical composition of claim 17 wherein $R^4$ and $R^5$ are hydrogen or $C_{1-6}$ alkyl; or a pharmaceutically acceptable derivative thereof.

28. The pharmaceutical composition of claim 27 wherein $R^4$ and $R^5$ are hydrogen or $C_{1-3}$ alkyl; or a pharmaceutically acceptable derivative thereof.

29. The pharmaceutical composition of claim 28 wherein $R^4$ and $R^5$ are $CH_3$; or a pharmaceutically acceptable derivative thereof.

30. The pharmaceutical composition of claim 17 wherein $R^6$ and $R^7$ are hydrogen or $CH_3$; or a pharmaceutically acceptable derivative thereof.

31. The pharmaceutical composition of claim 30 wherein $R^6$ and $R^7$ are hydrogen; or a pharmaceutically acceptable derivative thereof.

32. The pharmaceutical composition of claim 17 wherein said compound is selected from the group consisting of N-(4-(1,3-benzodioxol-5-yl)-3-{2-[(5-chloro-2-pyrimidinyl) oxy]ethoxy}-5-isoxazolyl)-4-(tert-butyl)benzenesulfonamide;

N-(4-(1,3-benzodioxol-5-yl)-3-{2-[(5-bromo-2-pyrimidinyl) oxy]ethoxy}-5-isoxazolyl)-4-(tert-butyl)benzenesulfonamide; and N-(4-(1,3-benzodioxol-5-yl)-3-{2-[(5-bromo-2-pyrimidinyl)oxy]ethoxy}-5-isoxazolyl)-4-(2-hydroxy-1,1-dimethylethyl)benzenesulfonamide; or a pharmaceutically acceptable derivative thereof.

* * * * *